United States Patent [19]

Hansen

[11] Patent Number: 5,290,795
[45] Date of Patent: Mar. 1, 1994

[54] SUBSTITUTED UREA COMPOUND AND USE

[75] Inventor: John B. Hansen, Jyderup, Denmark

[73] Assignee: Novo Nordisk N/A, Bagsvaerd, Denmark

[21] Appl. No.: 931,229

[22] Filed: Aug. 17, 1992

Related U.S. Application Data

[62] Division of Ser. No. 650,143, Feb. 4, 1991, Pat. No. 5,187,164.

[30] Foreign Application Priority Data

Feb. 16, 1990 [DK] Denmark ............................... 0408/90

[51] Int. Cl.$^5$ ..................... C07D 85/54; A61K 31/46
[52] U.S. Cl. ..................................... 514/305; 546/133
[58] Field of Search .................... 546/133; 514/305

[56] References Cited

U.S. PATENT DOCUMENTS

| Re. 29,556 | 2/1978 | Adelstein | 546/133 X |
|---|---|---|---|
| 4,003,904 | 1/1977 | Adelstein | 546/122 |
| 4,012,393 | 3/1977 | Markos et al. | 546/112 |
| 4,089,960 | 5/1978 | Gosteli et al. | 546/133 X |
| 4,797,387 | 1/1989 | King | 514/212 |
| 4,808,588 | 2/1989 | King | 514/212 |
| 4,863,921 | 9/1989 | Youssefyeh et al. | 546/133 X |
| 4,983,600 | 1/1991 | Ward et al. | 514/214 |

FOREIGN PATENT DOCUMENTS 0255297 2/1988 European Pat. Off. .

Primary Examiner—Marianne M. Cintins
Assistant Examiner—Catherine Scalzo
Attorney, Agent, or Firm—Steve T. Zelson; Elias J. Lambiris

[57] ABSTRACT

New substituted urea compounds of formula I, or a pharmaceutically acceptable salt thereof:

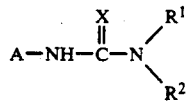

I wherein A is

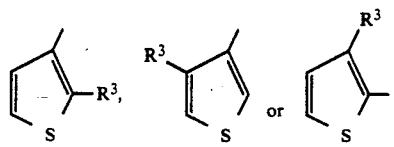

wherein $R^3$ is an oxadiazol, substituted with $C_{1-8}$-alkyl, $C_{2-8}$-alkenyl, $C_{2-8}$ alkynyl, $C_{3-7}$ cycloalkyl, benzyl, phenyl, $C_{1-6}$-alkoxy, $C_{1-6}$-alkylthio, amino or alkylamino;
$R^2$ is —H or lower alkyl;
X is O or S;
and $R^1$ is a group of formula II, III, IV or V

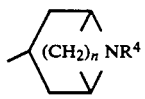

II

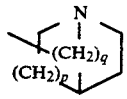

III

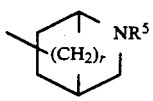

IV where n is 2 or 3, P is 1 or 2, q is 1 to 3, r is 1–3 and $R^4$ and $R^5$ are H, $C_{1-7}$ alkyl or $C_{3-6}$ cycloalkyl; and N-oxides thereof. The compounds are useful in pharmaceutical preparations for treating psychotic disorders, nausea and vomiting.

10 Claims, No Drawings

SUBSTITUTED UREA COMPOUND AND USE

This is a divisional application of co-pending application Ser. No. 07/650,143, filed Feb. 4, 1991 now U.S. Pat. No. 5,187,164.

The present invention relates to therapeutically active substituted urea compounds, a method of preparing the same, pharmaceutical compositions comprising the compounds, and a method of treating therewith.

EP158265 and EP235878 describes benzamides and substituted urea compounds having an azabicyclic side chain and possesing 5-HT antagonist activity.

A class of novel, structurally distinct compounds with higher 5HT$_3$-antagonist activity has now been discovered. These compounds have 5-HT$_3$-receptor antagonist activity, antiemetic activity and/or gastric motility enhancing activity. Furthermore, these compounds are useful for the treatment of cough and bronchoconstrictions.

The present invention provides a compound of formula I, or a pharmaceutically acceptable salt thereof:

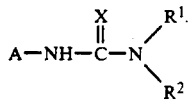

wherein A is

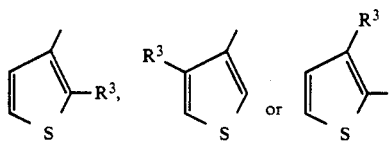

wherein R$^3$ is an oxadiazol, substituted with C$_{1-8}$-alkyl, C$_{2-8}$-alkenyl, C$_{2-8}$ alkynyl, C$_{3-7}$ cycloalkyl, benzyl, phenyl, C$_{1-6}$-alkoxy, C$_{1-6}$-alkylthio, amino or alkylamino;

R$^2$ is —H or lower alkyl;
X is O or S;
and R$^1$ is a group of formula II, III or IV

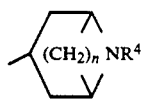 II

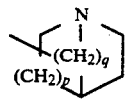 III

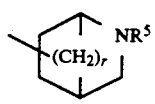 IV where n is 2 or 3, p is 1 or 2, q is 1 to 3, r is 1–3 and R$^4$ and R$^5$ are H, C$_{1-7}$ alkyl or C$_{3-6}$ cycloalkyl; and N-methylated ammonium derivatives thereof. Some of the compounds of the formula (I) have chiral or prochiral centres and are thus capable of existing in a number of stereoisomeric forms, including enantiomers. The invention extends to each of these stereoisomeric forms (including enantismers), and to mixtures thereof (including racemates). The different stereoisomeric forms may be separated one from the other by the usual methods. This invention furthermore extends to endo- and exo-configurations of compounds of formula (I).

The invention also provides a process for the preparation of a compound of formula (I), or a pharmaceutically acceptable salt thereof, which process comprises reacting a compound of formula V:

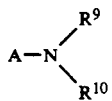 V with a compound of formula VI

 VI where R$^1$, R$^2$, R$^3$ are as defined above;

R$^9$ is COQ, where Q is a group displaceable by a nucleophile, R$^9$ and R$^{10}$ together =C=O, or R$^9$ is hydrogen (when R$^{10}$ is hydrogen); and when R$^9$ is COQ, or R$^9$—N—R$^{10}$ is N=C=O, J is NH$_2$ or NHR$^2$, or a reactive derivative thereof or when R$^9$ is hydrogen, J is a group containing an activated carbonyl group capable of forming a CO—N-linkage with the compound of formula (V) or Pharmaceutically acceptable salts of the compounds of this invention may be formed conventionally. The acid addition salts may be formed for example by reaction of the base compound of formula (I) with a pharmaceutically acceptable organic or inorganic acid.

Compounds of formula (I), which antagonise the effect of 5-HT at 5-HT$_3$ receptors, are useful in the treatment of conditions such as psychotic disorders (e.g. schizophrenia and mania); anxiety; panic disorders with and without agoraphobia, agoraphobia alone and obsessive compulsive disorders; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; and pain. Compounds of formula (I) may also be used in the treatment of dependency on drugs and substances of abuse, depression, and dementia and other cognitive disorders.

Unlike existing drug treatments for certain of the above conditions, the compounds of the invention, because of their high selectivity for 5-HT$_3$ receptors, would not be expected to produce undesirable side effects. Thus, for example, neuroleptic drugs may cause extrapyramidal effects, such as tardive dyskinesia, and benzodiazepines may cause dependence.

According to another aspect, the invention provides a method of treatment of a human or animal subject suffering from a psychotic disorder such as schizophrenia or mania; or from anxiety; nausea or vomiting, particularly that associated with cancer chemotherapy and radiotherapy; gastric stasis; symptoms of gastrointestinal dysfunction such as dyspepsia, reflux oesophagitis, peptic ulcer, flatulence and irritable bowel syndrome; migraine; pain; dependency on drugs or substances of abuse; depression; or dementia and other cognitive disorders which comprises administering an effective amount of a compound of formula (I) or a physiologically acceptable salt or solvate thereof. Furthermore, compounds of formula (I) may also be used in the treatment of cough and bronchoconstrictions.

Compounds of formula (i) were tested for their affinity to the 5HT$_3$-receptor using the following method:

5-HT3 Receptor Binding to N1E-115 Neuroblastoma Cells

The binding of 3H-quipazine to N1E-115 neuroblastoma cells in-vitro was determined by a modification of the method of Hoyer and Neijt (Hoyer, D. and Neijt, H. C., 1988, Molecular Pharmacology, 33:303–309). Mouse neuroblastoma cells of the clone N1E-115 were grown in Dulbecco's modified Eagle's medium with HEPES and Sodium bicarbonate (pH=7.6) as previously described. The cells were grown to a density of 8–15×10$^7$ cells per bottle and harvested by vigorous shaking. Harvested cells were homogenized in Tris buffer (20 mm, pH=7.5) containing 154 mM NaCl using a Brinkmann Polytron. The homogenate was centrifuged at 900×g and the supernatant was used directly in the binding assay. The supernatant was diluted at a concentration of 2×10$^6$ cells per ml in Tris buffer. Binding assays consisted of 50 μL 3H-Quipazine (1 nM final concentration), 250 μL membrane suspension, and 200 μL drug or buffer. Nonspecific binding was determined by the addition of 10 μM MDL 72222. Tubes were incubated at 370° C. for 60 minutes, followed by filtration through GFB filters under vacuum. The filters were then washed with ice-cold Tris buffer. Nonspecific binding represented approximately 12% of total binding.

RESULTS

Using the binding of 3H-Quipazine to 5-HT3 recognition sites located on N1E-115 neuroblastoma cells, a highly specific binding assay for the 5-HT3 receptor has been developed. The specificity for the 5-HT3 receptor site is shown by the inability of 8-OH-DPAT (a specific ligand for the 5-HT1A receptor), and ketanserin (a specific ligand for the 5-HT2 receptor) to displace 3H-Quipazine. Furthermore, ligands known to specifically bind to the 5-HT3 receptor (quipazine, ICS 205-930, zacopride and MDL 72222) are potent displacers of 3H-Quipazine binding.

The compounds of the present invention gave the following results (Table 1):

TABLE 1

| Example | IC$_{50}$ (nM) |
|---------|----------------|
| 4 | 6.7 |
| 7 | 2.3 |

Inhibition of 5-HT-Induced Contractions in Isolated Guinea Pig Ileum

Compounds of formula (I) were tested for their 5HT$_3$-antagonist activity using the following method:
Principle 5-HT produces contractions of the guinea pig ileum via 2 different receptors. 1) direct contractions via 5-HT$_2$ receptors on the muscle, 2) indirect contractions via 5-HT$_3$ receptors on intrinsic gut neurones, producing acetylcholine release. By administering 5-HT to lengths of ileum in the presence of methysergide (to block 5-HT$_2$ receptors) you can assay 5-HT$_3$ receptor activity.
Method Guinea pigs were killed by means of cervical dislocation the terminal 15 cm of ileum removed, and 1.5–2.0 cm lengths prepared and mounted in 10 ml organ baths containing calcium deficient tyrodes of the following composition (mM) NaCl (136.9); KCl (2.68); CaCl$_2$ (0.9); MgCl$_2$(1.05); NaCO$_3$ (11.9); NaH$_2$PO$_4$(0.42); glucose (5.55) and containing methysergide (10$^{-6}$M) maintained at 37° C. and gassed with 95% O$_2$ and 5% CO$_2$. The mechanical activity of the muscle was measured by a HSE 351 isometric transducer connected via a HSE bridge amplifier to a potentiometric pen recorder. Resting tension was 1 g and the tissue left to equilibrate for 1 hour.

First a dose response curve is obtained to acetylcholine on each tissue. Then one tissue is incubated for 20 min with tyrode and three with tyrode plus the putative 5-HT$_3$ antagonist. After this incubation dose response curves to 5-HT are constructed to 5-HT in all 4 tissues (one control 3+test drug). Contact time for 5-HT 30 sec.

Results

The maximum response to acetylcholine for each tissue is measured and the responses to 5-HT calculated as percentage maximum of the acetylcholine (Ach) maximum response in that tissue. The peak of the 5-HT response is measured.

For each tissue the concentration of 5-HT giving 100% of the maximum acetylcholine response (measured at 30 sec) is quoted.

The effect of a drug is quantified as the ratio of the concentration of 5-HT producing a 100% maximal Ach response in the presence and absence of the antagonist (dose ratio). The figure quoted is the concentration of the antagonist giving a dose ratio of 2, (A$_2$).

By testing some compounds of the invention the following results were obtained (A$_2$mg/ml): example 4 (0.04), example 7 (0.01).

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compound of the invention is dispensed in unit dosage form comprising 0.05–100 mg in a pharmaceutically-acceptable carrier per unit dosage.

A typical tablet which may be prepared by conventional tabletting techniques contains:

| Active compound | 1.0 mg |
| --- | --- |
| Lactosum | 67.9 mg ph. Eur. |
| Avicel ® | 31.4 mg |
| Amberlite ® IRP 88 | 1.0 mg |
| Magnesii stearas | 0.25 mg Ph. Eur. |

The invention will now be described in further detail with reference to the following examples:

EXAMPLE 1

3-Amino-2-(3-butyl-1,2,4-oxadiazol-5-yl)thiophene

In 30 ml dry ethanol containing 2 g powdered molecular sieves was dissolved under nitrogen at room temperature 0.6 g sodium. n-butylcarboxamidoxim (4.0 g, 35 mmol) was added and the mixture was stirred for 10 min. after which methyl 3-aminothiophene-2-carboxylate (3.1 g, 20 mmol) was added. The mixture was refluxed for 1 hour and then stirred at 70°0 C. for 20 hours, cooled to room temperature and filtered through decalite. The filtrate was concentrated in vacuo and the resulting oil purified by filtration through a short path of silica gel with methylene chloride as eluent giving 3.4 g. M.p. 69°–70° C.

EXAMPLE 2

3-Amino-2-(3-cyclopropyl-1,2,4-oxadiazol-5-yl)-thiophene

In 50 g dry ethanol containing 3 g powdered molecular sieves was dissolved under nitrogen at room temperature 0.8 g sodium. Cyclopropylcarboxamidoxim (3.5 g, 35 mmol) was added and the mixture was stirred for 10 min. after which methyl 3-aminothiophene-2-carboxylate (4.7 g, 30 mmol) was added. The mixture was refluxed for 16 hours, cooled to room temperature, filtered through decalite and concentrated in vacuo. The residue was taken up in water and ethylacetate and the organic phase was washed with saturated sodium chloride and dried with magnesium sulfate. Evaporation of the solvent gave 4.9 g of the desired product as. M.p. 51°–54° C.

EXAMPLE 3

N-(2-(3-Cyclopropyl-1,2,4 oxadiazol-5-yl)-3-thienyl)-$N^1$-(endo-9-methyl-9-azabicyclo[3.3.1]non-3-yl)thiourea 3-Amino-2-(3-cyclopropyl-1,2,4-oxadiazol-5-yl)-thiophene (1.0 g, 5 mmol) in 10 ml dry methyl was added dropwise to a rigorously stirred mixture of thiophosgene (0.5 ml, 6.5 mmol) in 10 ml $H_2O$. Upon addition 1.0 ml triethylamine was added and stirring was continued for 20 min. whereupon the organic phase was isolated. The aqueous phase was washed with methylene chloride. To the combined organic phases were added endo3-amino-9-methyl-9-azabicyclo[3.3.1]nonan (0.9 g, 6 mmol) in 5 ml methylene chloride. The mixture was stirred at room temperature for 2 hours. 5 ml saturated sodium bicarbonate was added. The product isolated by filtration, washed with water and dried. Upon washing with warm acetone was isolated 1.3 g of the desired product. M.p. 205°–206° C.

EXAMPLE 4

N-(2-(3-Cyclopropyl-1,2,4-oxadiazol-5-yl)-3-thienyl)-$N^1$- (endo-9-methyl-9-azabicyclo[3.3.1]non-3yl)urea To phosgene (7.5 ml, 1.9M in toluene) dissolved in 25 ml dry methylene chloride stirred at 0° C. under nitrogen was added dropwise 3-amino-2-(3-cyclopropyl-1,2,4-oxadiazol-5-yl)thiophene (1.3 g, 2.3 mmol) in 25 ml methylene chloride. After half of the addition was completed, triethylamine (1.8 ml, 12 mmol) was added. Upon completion of the additions the mixture was stirred at room temperature for 2 hours. The solvent was evaporated off. The residue was redissolved in methylene chloride and the solvent evaporated off again. The residue was dissolved in 25 ml methylene chloride and 2 ml triethylamine and stirred at 0° C. whereupon endo-3-amino-9-methyl-9-azabicyclo[3.3.1-]nonane (1.2 g, 7.5 mmol) in 25 ml methylene chloride was added and the mixture stirred for 16 hours at room temperature. The mixture was then washed with saturated sodium bicarbonate, water and saturated sodium bicarbonate, water and saturated sodium chloride, dried over magnesium sulfate and concentrated in vacuo. The resulting crystals were washed with acetone to give 1.2 g of the desired product. M.p. 187°–188° C.

EXAMPLE 5

N-(2-(3-cyclopropyl-1,2,4-oxadiazol-5-yl)-3-thienyl)-$N^1$-(3-quinuclidinyl)thiourea 3-Amino-2-(3-cyclopropyl-1,2,4-oxadiazol-5-yl)thiophene (1.0 g, 5 mmol) in 10 ml dry methylene chloride was added dropwise to a vigorously stirred mixture of thiophosgene (10.5 ml, 6.5 mmol) in 10 ml $H_2O$. Upon addition 1.0 ml triethylamine was added and stirring continued for 20 min. whereupon the organic phase was isolated and the aqueous phase was washed with methylene chloride. The combined organic phases were added to a solution of 3-aminoquinuclidine, dihydrochloride (1.2 g, 6 mmol) dissolved in 1 ml $H_2O$ and made alkaline with 50% NaOH. This mixture was then stirred at room temperature for 6 hours whereupon 5 ml saturated sodium bicarbonat was added. The desired product was isolated by filtration, washed with water and dried to give 0.2 g. M.p. 155°–157° C.

EXAMPLE 6

N-(2-(3-Butyl-1,2,4-oxadiazol-5-yl)-3-thienyl)-N¹-(endo-9-methyl-9-azabicyclo[3.3.1]non-3-yl)thiourea N-(2-(3-Butyl-1,2,4-oxadiazol 5-yl)thiophene (0.6 g, 2.65 mmol) in 5 ml dry methylene chloride was added dropwise to a rigorously stirred mixture of thiophosgene (0.3 ml, 3.9 mmol) in 5 ml H₂O. Upon addition 0.5 ml triethylamine was added and stirring continued for 30 minutes whereupon the organic phase was isolated. The aqueous phase was extracted with methylene chloride. The combined organic phases were added to a solution of endo-3-amino-9-methyl-9-azabicyclo[3.3.1]nonan in 5 ml methylene. The mixture was stirred for 1 hour at room temperature and then washed with saturated sodium bicarbonate, water and saturated sodium chloride, dried over magnesium sulfate and concentrated in vacuo. The resulting crystals were washed with acetone and methanol to give 650 mg of the desired product. M.P. 171°–172° C.

EXAMPLE 7

N-(2-(3-Butyl-1,2,4-oxadiazol-5-yl)-3-thienyl)-N¹-(endo-9-methyl-9-azabicyclo[3.3.1]non-3-yl)urea 3-Amino-2-(3-butyl-1,2,4-oxadiazol-5-yl)thiophene (0.9 g, 4 mmol) in 30 ml dry methylene chloride was added dropwise to a stirred mixture of phosgene (5.3 ml, 1.9M in toluene) and 30 ml dry methylene chloride under nitrogen at 0° C. After 15 ml of the solution was added, 1.4 ml triethylamine was added. Upon completion of the addition the mixture was stirred at room temperature for 2 hours and then concentrated in vacuo. The resulting oil was redissolved in methylene chloride and reevaporated. The product was dissolved in 25 ml dry methylene chloride and 1.4 ml triethylamine and stirred at 0° C. Endo-3-amino-9-methyl-9-azabicyclo[3.3.1]nonane (1.0 g, 6.3 mmol) was added whereupon the mixture was stirred at room temperature for 16 hours. The mixture was washed with saturated sodium bicarbonate, water and saturated sodium chloride, dried over magnesium sulphate and concentrated in vacuo. Upon washing with methanol 0.2 g of the desired product was isolated. M.p. 220°–223° C.

EXAMPLE 8

N-(2-(3-Butyl-1,2,4-oxadiazol-5-yl)-3-thienyl)-N¹-(3-quinuclidinyl) thiourea, oxalate 3-Amino-2-(3-butyl-1,2,4-oxadiazol-5-yl)-thiophene (0.6 g, 2.6 mmol) in 5 ml methylene chloride was added dropwise to a rigorously stirred mixture of thiophosgene (0.3 ml, 3.9 mmol) in 2.5 ml water. 0.5 ml triethylamin was added and stirring continued for additional 30 minutes whereupon the phases were separated. The aqueous phase was extracted with methylene chloride. To the combined organic phases were added a solution of 3-aminoquinuclidine dihydrochloride (1.1 g, 6 mmol) in 5 ml water which was made alkaline with 4N NaOH. The mixture was stirred for 16 hours and then washed with saturated sodium bicarbonate, water, and saturated sodium chloride. After evaporation of the solvent the product was purified by colomn chromatography (silica gel, merck 60, methylene chloride, methanol, concentrated amonium hydroxide; 90:10:0.5 (V/V/V)). The product was dissolved in acetone and precipitated as the oxalate by addition of oxalic acid. Yield: 0.12 g. M.p. 174°–175° C.

I claim:

1. A compound of formula I:

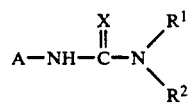

wherein
A is

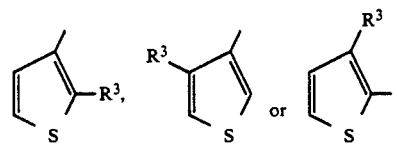

wherein
R³ is a 1,2,4-oxadiazole substituted with $C_{1-8}$-alkyl, $C_{2-8}$-alkenyl, $C_{2-8}$-alkynyl, $C_{3-7}$-cycloalkyl, benzyl, phenyl, $C_{1-6}$-alkoxy, $C_{1-6}$-alkylthio or amino;
R² is H or lower alkyl;
X is O or S; and
R¹ is a group of formula III

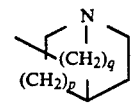

wherein
p is 1 and q is 2; or
an N-methylated ammonium derivative thereof.

2. The compound according to claim 1, wherein X is S.

3. The compound according to claim 1, wherein R² is H.

4. The compound according to claim 1, wherein R³ is a 1,2,4-oxadiazole substituted with $C_{1-6}$-alkyl.

5. The compound according to claim 1, wherein X is S, R² is H and R³ is an oxadiazol substituted with $C_{1-6}$-alkyl.

6. The compound according to claim 1 which is
N-(2-(3-cyclopropyl-1,2,4-oxadiazol-5-yl)-3-thienyl)-N¹-(3-quinuclidinyl)thiourea;
N-(2-(3-butyl-1,2,4-oxadiazol-5-yl)-3-thienyl)-N¹-(3-quinuclidinyl)thiourea; or
and N-methylated ammonium derivative thereof.

7. A pharmaceutical composition comprising as an active ingredient, a compound according to claim 1 and a pharmaceutically-acceptable carrier or diluent.

8. The pharmaceutical composition according to claim 7 which contains between 0.1 mg and 250 mg of the active ingredient per dose unit.

9. A method of treating schizophrenia, mania, anxiety or panic disorders in a subject in need thereof comprising administering an effective amount of a compound according to claim 1.

10. A method of treating schizophrenia, mania, anxiety or panic disorders in a subject in need thereof comprising administering a pharmaceutical composition according to claim 7.

* * * * *